United States Patent [19]

Sawaya

[11] Patent Number: 4,969,554
[45] Date of Patent: Nov. 13, 1990

[54] DISPOSABLE SHARP INSTRUMENT CONTAINER

[76] Inventor: Frederick J. Sawaya, 24657 W. 10 Mile Rd., #2, Southfield, Mich. 48034

[21] Appl. No.: 474,895

[22] Filed: Feb. 5, 1990

[51] Int. Cl.$^5$ ............................................. B65D 83/10
[52] U.S. Cl. ..................................... 206/370; 206/366; 206/210; 220/1 T; 229/128; 229/907
[58] Field of Search ............... 206/364, 366, 370, 210; 220/1 T, 229, 339; 229/125.02, 128, 907; 232/43.1, 43.2, 43.5, 44, 48

[56] References Cited

U.S. PATENT DOCUMENTS

| | | | |
|---|---|---|---|
| 2,962,155 | 11/1960 | Rusciano . | |
| 2,971,688 | 2/1961 | Akers | 229/907 |
| 2,990,059 | 6/1961 | Hitt . | |
| 3,080,087 | 3/1963 | Cloyd | 220/339 |
| 3,148,822 | 9/1964 | Yochum, Jr. | 220/339 |
| 3,900,550 | 8/1975 | Oliver et al. | 220/339 |
| 4,009,818 | 3/1977 | Rogers | 232/43.1 |
| 4,037,754 | 7/1977 | Wilhelmi et al. | 220/229 |
| 4,040,419 | 8/1977 | Goldman . | |
| 4,106,621 | 8/1978 | Sorenson . | |
| 4,121,755 | 10/1978 | Meseke et al. | 206/366 |
| 4,270,536 | 6/1981 | Lemelson . | |
| 4,273,123 | 6/1981 | Lemelson . | |
| 4,315,592 | 2/1982 | Smith | 206/370 |
| 4,328,904 | 5/1982 | Iverson | 220/229 |
| 4,375,849 | 3/1983 | Hanifl . | |
| 4,452,358 | 6/1984 | Simpson . | |
| 4,520,926 | 6/1985 | Nelson . | |
| 4,600,112 | 7/1986 | Shillington et al. . | |
| 4,679,700 | 7/1987 | Tharrington et al. | 220/1 T |
| 4,722,472 | 2/1988 | Bruno | 206/366 |
| 4,804,090 | 2/1989 | Schuh et al. . | |
| 4,816,307 | 3/1989 | Honeycutt . | |
| 4,840,272 | 6/1989 | Goldman . | |
| 4,848,569 | 7/1989 | Leishman . | |
| 4,900,500 | 2/1990 | Honeycutt | 264/263 |

*Primary Examiner*—David T. Fidei
*Attorney, Agent, or Firm*—Dykema Gossett

[57] ABSTRACT

Containers are disclosed for storing soiled sharp medical instruments. In one embodiment, a container has an entrance defined by a pair of flaps. A soiled medical instrument is positioned on one of the flaps and pushed downwardly such that the flaps move apart allowing access to the container for storing the medical instrument. The container is preferably formed of a clear plastic material such that medical personnel may count the number of instruments stored within the container. A second embodiment includes a cylindrical member with a plate positioned near one axial end such that an enlarged space and a smaller space are defined. Both embodiments allow entire syringes to be easily stored while still providing safe storage of smaller medical instruments such as suture needles.

12 Claims, 2 Drawing Sheets

DISPOSABLE SHARP INSTRUMENT CONTAINER

BACKGROUND OF THE INVENTION

The present invention relates to a device for receiving used syringes, suture needles, scalpels and other sharp medical instruments.

In modern medical environments, it is of the utmost importance that medical personnel not be exposed to soiled syringes or other sharp medical instruments which may be contaminated by disease. In the past, medical personnel have been accidentally punctured or cut by these soiled sharp medical instruments.

This problem has become particularly acute with recent concern about such highly contagious and dangerous diseases as the AIDS virus. With all of these concerns, an operating environment still requires that many steps be taken promptly and it is not always possible to keep soiled sharp instruments safely removed from medical personnel. For this reason, the prior art developed containers to receive soiled sharp medical instruments.

Many prior art containers are large central containers disposed on a wall of the operating room. Medical personnel must transport the soiled sharp medical instruments to the wall-mounted container to dipose of them. This leaves the potentially infectious sharp instruments exposed to medical personnel at the operating site until transported to the container. In addition, medical personnel who must transport soiled instruments to the container on the wall are exposed to being punctured or cut by the instruments.

Several smaller disposable needle container have been disclosed in the prior art but are inadequate for a number of reasons. Many do not provide sufficient room to receive an entire syringe or other elongate instruments, such as scalpels.

Some prior art containers do not smoothly guide sharp instruments into a stored position. With these types of containers, medical personnel may be cut while attempting to dispose of the sharp instruments by placing them in the container.

Several prior art devices are opaque and do not provide medical personnel with the ability to view the interior of the container. The number of instruments within a container cannot be counted. In an operating environment, medical personnel have an accurate idea of the number of instruments that have been utilized. Thus, it is desirable to count the number of instruments received within a container to determine that there are no stray soiled instruments left out and exposed.

It is thus an object of the present invention to disclose an improved container for receiving soiled sharp medical instruments that provides sufficient space such that elongate instruments such as an entire syringe, or a scalpel, can be received within the container.

It is further an object of the present invention to diclose a container in which soiled medical instruments that are placed in the container are easily guided into the container.

It is further an object of the present invention to disclose a container in which the number of soiled instruments within the container can be counted.

SUMMARY OF THE INVENTION

The present invention discloses a container for receiving soiled and discarded syringes, suture needles, scalpels or any other sharp medical instrument. More particularly, a first embodiment of the present invention discloses a container with longitudinal and lateral sides, a top and a bottom defining an interior space for receipt of soiled sharp medical instruments.

The top includes two flap members that overlap and define an entrance to the interior space. One of the flaps is snapped beneath a latch member and the other flap is received vertically beneath the first flap. The second flap is biased upwardly into the first flap thus normally maintaining the entrance to the interior space closed. When it is desired to place a sharp medical instrument into the container, medical personnal simply place the instrument upon the second flap and push downwardly. The sharp medical instrument is guided along the second flap beneath the first flap and falls into the space within the container.

In a preferred embodiment of the present invention, the second flap is formed with a first generally planar portion and a second generally planar portion extending vertically upwardly at an angle from the first portion. This second portion underlies the first flap and provides a ledge for receipt of the sharp medical instrument, guiding it into the container.

In a preferred embodiment of the present invention, the flaps are formed integrally with the molded container and are connected to the longitudinal sides through living hinges. At least one wall, and preferably the entire container, is formed of clear plastic such that the interior space may be viewed to allow counting of the number of sharp medical instruments within the container.

In a most preferred embodiment of the present invention, a sterilizing material is disposed within the interior space to decontaminate soiled medical instruments as they are received within the container.

A second embodiment of the present invention includes an elongate cylindrical member defining a first enlarged space and a second smaller space. A wall within the cylindrical member separates the two spaces. The enlarged space receives elongate medical instruments such as syringes or scalpels, while the smaller space receives smaller medical instruments such as suture needles. Each space is closed by a cap member that is snapped over the cylindrical member. Each space includes a needle retaining material, such as foam, into which the sharp medical instruments are inserted.

In a most preferred embodiment, this needle retaining material includes sterilizing fluid to neutralize any contaminants on the soiled medical instruments.

Both embodiments are relatively inexpensive and can be disposed of after use.

These and other objects and features of the present invention can be best understood from the following specification and drawings, of which the following is a brief description.

DETAILED DESCRIPTION OF PREFERRED EMBODIMENT

Figure 1:
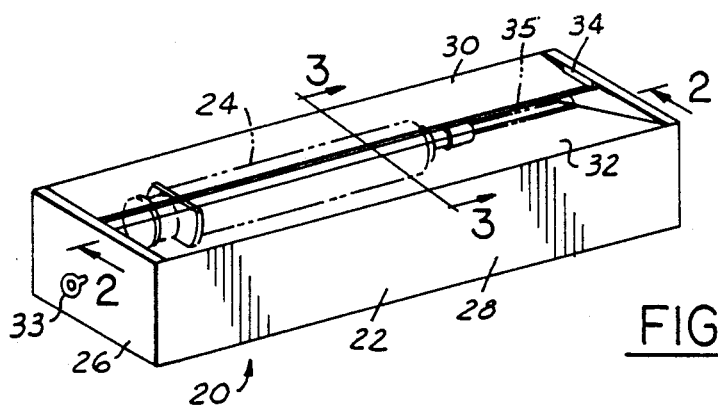
FIG. 1 is a perspective view of a first embodiment of the present invention.

A first embodiment 20 of the present invention is illustrated in FIG. 1. Container 22 receives sharp medical instruments such as syringe 24. Container 22 may receive any other type of sharp medical instrument such as suture needles, scalpels, or any other type of medical instrument that may be soiled. Container 22 includes lateral walls 26 and longitudinal walls 28. First flap 30 and second flap 32 define a top to container 22. First flap 30 is snapped beneath latch 34 while second flap 32 is snapped beneath first flap 30. Latch 24 is also above second flap 32 and prevents it from moving too far upwardly should it move past first flap 30. Second flap 32 is normally biased upwardly into first flap 30 such that a normally closed entrance 35 to the interior space within container 22 is defined between first flap 30 and second flap 32.

Eyelet hook, or loop 33 is provided on a lateral wall and receives a strap such that container 22 can be attached to a belt, or any other carrying aid.

Figure 2:
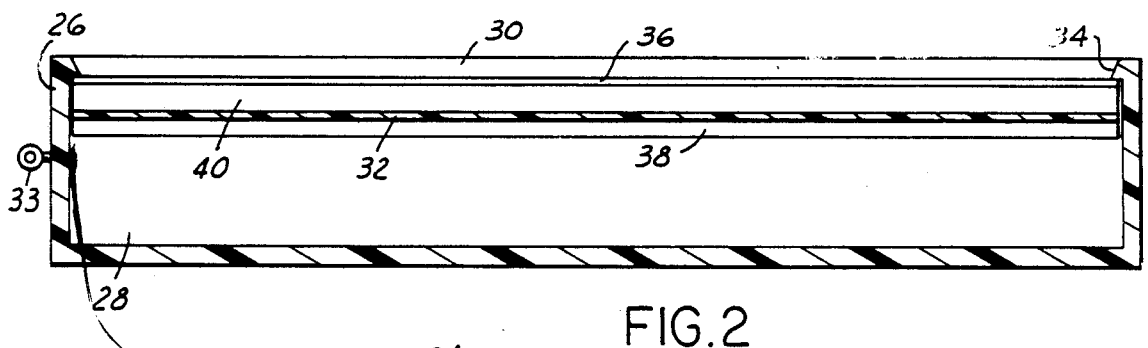
FIG. 2 is a cross-sectional view along line 2—2 as shown in FIG. 1.

As shown in FIG. 2, container 22 includes lateral walls 26 and longitudinal walls 28. First flap 30 has end 36 snapped beneath latch 34 at each longitudinal end. Second flap 32 includes a first generally planar portion 38 extending from a longitudinal wall 28 laterally inwardly. A second generally planar portion 40 extends vertically upwardly at an angle from first planar section 38 and underlies first flap 30.

Figure 3:
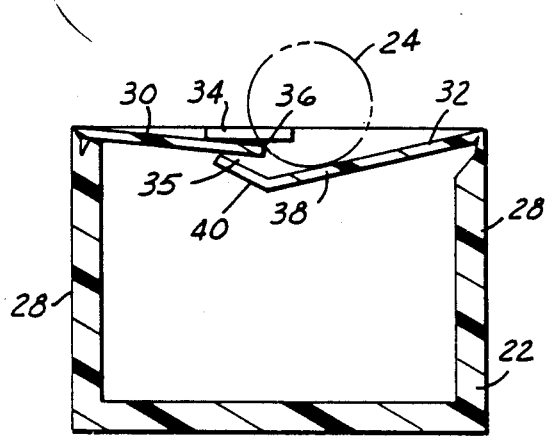
FIG. 3 is a cross-sectional view along line 3—3 as shown in FIG. 1.

As shown in FIG. 3, when it is desired to place sharp medical instruments such as syringe 24 within container 22 it is initially placed upon first planar portion 38 of second flap 32. Medical personnel then push lightly downwardly upon syringe 24 and second flap 32 moves counterclockwise, as orientated in FIG. 3, such that syringe 24 is guided onto second portion 40, which provide a ledge to support syringe 24. The second portion 40 helps syringe 24 be smoothly guided in the interior space without twisting or lurching and possibly cutting the medical personnel.

Figure 4:
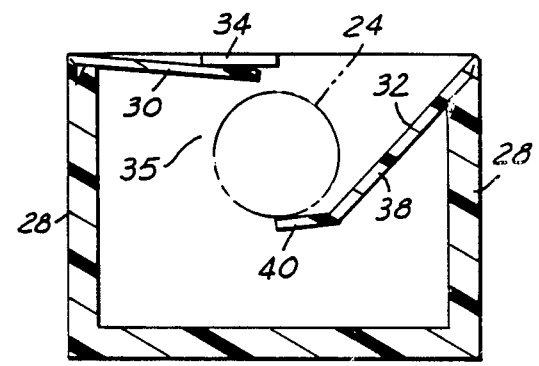
FIG. 4 is a view similar to FIG. 3.

As shown in FIG. 4, as second flap 32 moves counterclockwise, entrance 35 opens and allows syringe 24 access to the space within container 22. Syringe 24 is illustrated resting on second portion 40. As second flap 32 continues to move counterclockwise, second portion 40 begins to guide syringe 24 vertically downwardly into the space within container 22.

A method of storing a smaller sharp instrument, such as suture needles within container 22 will now be explained. The suture needles are grasped by an instrument such as forceps and placed upon second flap 32. The instrument is pushed downwardly against second flap 32 which rotates counterclockwise providing access to the space within container 22. The instrument used to hold the suture needle is now released and the needle falls into container 22.

Figure 5:
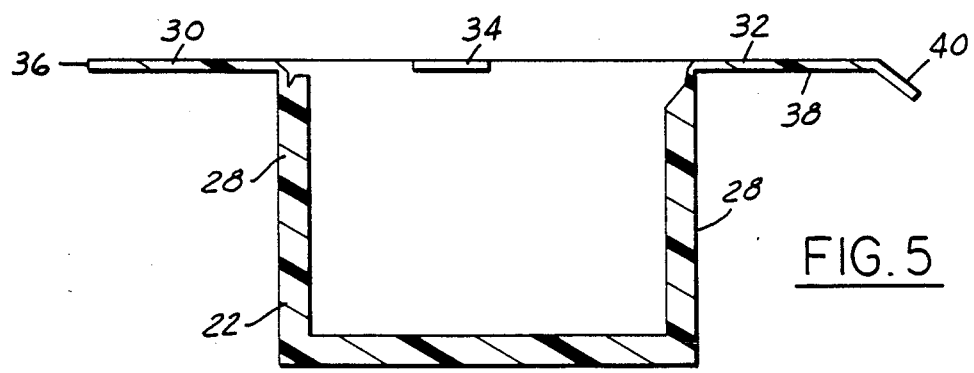
FIG. 5 is a cross-sectional view similar to FIG. 3 but showing the flap members of the present invention in a non-working position.

As shown in FIG. 5, container 22 is a one-piece molded item with flaps 30 and 32 being connected to longitudinal walls 28 through living hinges. In a most preferred embodiment of the present invention, at least one wall, and preferably the entire container, is formed of clear plastic such that medical personnel can count the number of soiled medical instruments received within container 22.

Figure 6:
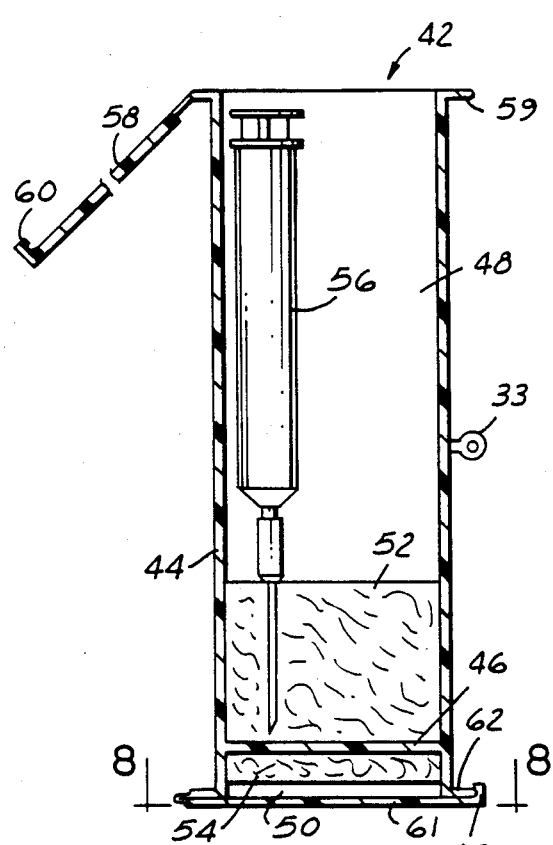
FIG. 6 is a cross-sectional view showing a second embodiment of the present invention.

A second embodiment 42 of a container is illustrated in FIG. 6 and includes cylindrical body 44 having wall 46 near one axial end defining enlarged space 48 and smaller space 50. Enlarged space 48 includes needle retaining material 52, such as foam, and receives elongate medical instruments such as syringe 56 or scalpels. Enlarged space 48 is covered by cap 58 which is secured to ledge 59 of cylindrical member 44 by ears 60. When it is desired to dispose an elongate medical instrument, such as syringe 56, within enlarged space 48, cap 58 is snapped off ledge 59, thus providing access to enlarged space 48.

Figure 7:
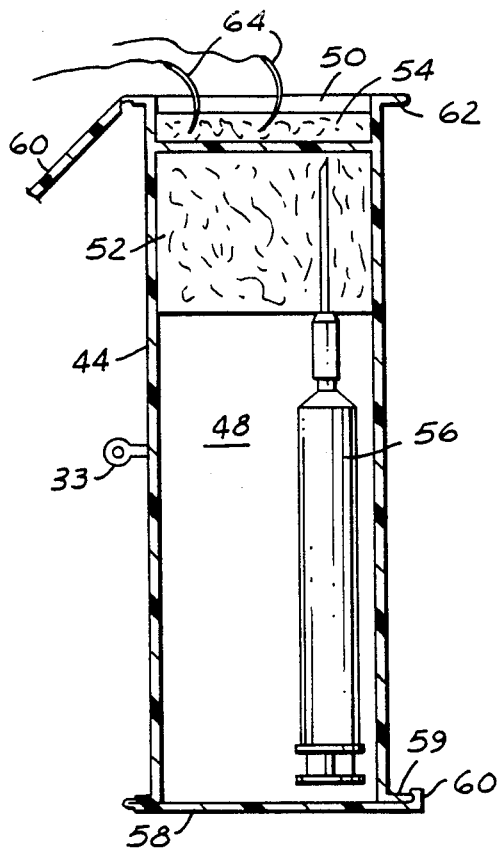
FIG. 7 is a view similar to FIG. 6 showing the second embodiment of the present invention.

Second cap 61 covers smaller space 50 and is secured to second ledge 62 of cylindrical member 44 by ears 63. As shown in FIG. 7, when it is desired to dispose smaller items, such as suture needles 64 in container 42 cap 61 is opened to provide access to smaller space 50. Smaller items such as suture needles 64 can be placed in needle retaining material 54.

With this device any size sharp medical intsruments can be received in a relatively small device that is both portable and easy to utilize. Perferably, container 42 is formed of clear plastic such that the number of instruments within spaces 48 and 50 can be easily counted.

Most preferably, this plastic is polypropylene, which is a FDA approved material.

Figure 8:
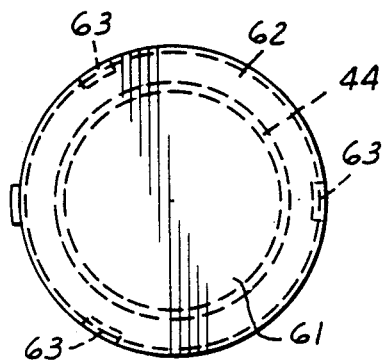
FIG. 8 is a cross-sectional view along line 8—8 as shown in FIG. 6.
Figure 9:
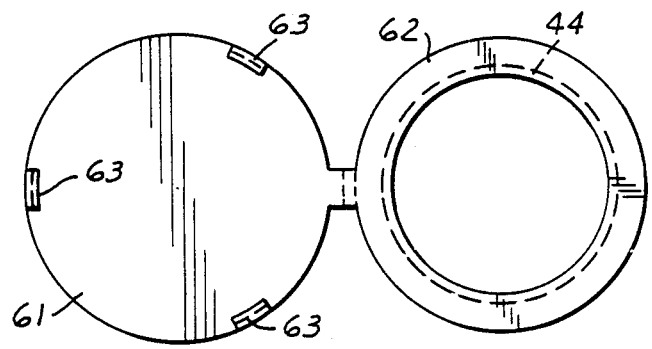
FIG. 9 is a view similar to FIG. 8.

Details of cap 61 are shown in FIG. 8. Cap 61 is secured to ledge 62 by ears 63. As shown in FIG. 9, ears 63 extend radially inwardly on an inner side of cap 61.

Both disclosed embodiments are inexpensive and disposable after use.

Preferred embodiments of the present invention have been disclosed, however, a worker of ordinary skill in the art would realize that certain modifications would be within the scope of this invention and thus the following claims should be studied in order to determine the true scope and content of the invention.

I claim:

1. A device for receiving soiled sharp medical instruments comprising:
   a container having longitudinal and lateral walls, a top and a bottom defining a space for receipt of soiled medical instruments;
   said top including first and second flaps, an entrance to said space defined between said flaps;
   said first flap overlying a portion of said second flap thus normally closing said entrance;
   a latch is defined on said container, said first flap being snapped beneath said latch, said second flap being biased upwardly against said first flap;
   said first and second flaps being integrally connected to said container by living hinges;
   said second flap having a first generally planar portion and a second generally planar portion extending vertically upwardly at an angle from said first portion, said second generally planar portion underlying said first flap.

2. A device as recited in claim 1, wherein said first and second flaps being connected to the longitudinal sides of said container.

3. A device as recited in claim 2, wherein at least one wall of said container being formed of clear plastic affording a view of the interior of said container.

4. A device as recited in claim 3, wherein a sterilizing material is disposed within said space.

5. A device for receiving soiled sharp medical instruments comprising:
    a container having longitudinal and lateral walls, a top and a bottom defining a space for receipt of soiled medical instruments;
    said top including first and second flaps, an entrance to said space defined between said flaps;
    said first flap overlying a portion of said second flap thus normally closing said entrance;
    said second flat having a first generally planar portion and a second generally planar portion extending vertically upwardly at an angle from said first portion, said second generally planar portion underlying said first flap.

6. A device as recited in claim 5, wherein a latch is defined on said container, said first flap being snapped beneath said latch, and said second flap being biased upwardly against said first flap.

7. A device as recited in claim 6, wherein said latch extends longitudinally inwardly from each lateral wall, and extends laterally beyond said first flap.

8. A device as recited in claim 6, wherein said first and second flaps are integrally connected to said container by living hinges.

9. A device as recited in claim 6, wherein said first and second flaps are hinged to said longitudinal walls of said container, said longitudinal walls being longer and the average length of a standard syringe.

10. A device as recited in claim 6, wherein said first and second flaps are integrally connected to said container by a living hinge.

11. A device as recited in claim 6, wherein at least one wall of said container is formed of clear plastic.

12. A device as recited in claim 6, wherein a sterilizing material is disposed within said space.

* * * * *